(12) United States Patent
Della Santina et al.

(10) Patent No.: US 8,768,484 B2
(45) Date of Patent: Jul. 1, 2014

(54) HIGH-VOLTAGE CMOS NEUROELECTRONIC INTERFACE FOR A MULTICHANNEL VESTIBULAR PROSTHESIS

(75) Inventors: Charles Coleman Della Santina, Towson, MD (US); Andreas Andreou, Baltimore, MD (US); Zaven Kalayjian, Gaithersburg, MD (US); Gene Fridman, Baltimore, MD (US); Bryce Chiang, Baltimore, MD (US); Julius Georgiou, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/812,107

(22) PCT Filed: Jul. 26, 2011

(86) PCT No.: PCT/US2011/045384
§ 371 (c)(1),
(2), (4) Date: Jan. 24, 2013

(87) PCT Pub. No.: WO2012/018631
PCT Pub. Date: Feb. 9, 2012

(65) Prior Publication Data
US 2013/0131761 A1    May 23, 2013

Related U.S. Application Data

(60) Provisional application No. 61/367,474, filed on Jul. 26, 2010.

(51) Int. Cl.
*A61N 1/05*    (2006.01)
(52) U.S. Cl.
USPC .......................................... 607/62

(58) Field of Classification Search
USPC .......................................... 607/62
See application file for complete search history.

(56) References Cited

U.S. PATENT DOCUMENTS

| 6,638,208 | B1 | 10/2003 | Natarajan et al. |
| 7,613,519 | B2 * | 11/2009 | De Ridder ..................... 607/55 |
| 2003/0149450 | A1 * | 8/2003 | Mayberg ......................... 607/3 |
| 2006/0241718 | A1 | 10/2006 | Tyler et al. |
| 2007/0250119 | A1 | 10/2007 | Tyler et al. |
| 2009/0306458 | A1 | 12/2009 | Parker et al. |
| 2009/0306741 | A1 | 12/2009 | Hogle et al. |
| 2009/0312817 | A1 | 12/2009 | Hogle et al. |
| 2010/0174329 | A1 | 7/2010 | Dadd et al. |
| 2010/0174330 | A1 | 7/2010 | Dadd et al. |
| 2010/0174344 | A1 | 7/2010 | Dadd et al. |

FOREIGN PATENT DOCUMENTS

| AU | 1999/059093 | 4/2000 |
| AU | 2001/071936 | 2/2002 |
| WO | WO-2000/015140 A1 | 3/2000 |
| WO | WO-02/09363 A2 | 1/2002 |
| WO | WO-2008/052166 A2 | 5/2008 |
| WO | WO-2008/052166 A3 | 7/2008 |

OTHER PUBLICATIONS

International Search Report and Written Opinion of PCT/US2011/045384.
Carey et al., "Principles of applied vestibular physiology.,". Cummings, Ed. Elsevier, 2005.
Chiang et al., "Enhancements to the Johns Hopkins Multi-Channel Vestibular Prosthesis Yield Reduced Size, Extended Battery Life, Current Steering and Wireless Control," presented at Association for Research in Otolaryngology Abst. 867, Baltimore, MD 2009.
Constandinou et al., "A fully-integrated semicircular canal processor for an implantable vestibular prosthesis," IEEE, St. Julien's: 2008.
Constandinou et al., "A micropower tilt processing circuit," IEEE, Baltimore, MD: 2008.
Constandinou et al., "A Neural Implant ASIC for the Restoration of Balance in Individuals with Vestibular Dysfunction," IEEE, 2009.
Constandinou et al., "A Partial-Current-Steering Biphasic Stimulation Driver for Vestibular Prostheses," Biomedical Circuits and Systems, IEEE Transactions on, vol. 2, No. 2 2008.
Constandinou et al., "An ultra-low-power microoptoelectromechanical tilt sensor," IEEE, Seattle, WA: 2008.

Constandinou et al., "Towards an Implantable Vestibular Prosthesis: The Surgical Challenges," IEEE EMBS Conference on Neural Engineering, Kohala Coast, HI: 2007.

Davidovics et al., "Effects of biphasic current pulse frequency, amplitude, duration and interphase gap on eye movement responses to prosthetic electrical stimulation of the vestibular nerve," IEEE Trans Neural Syst Rehabil Eng. Feb. 2011;19(1):84-94.

Della Santina et al., "A multichannel semicircular canal neural prosthesis using electrical stimulation to restore 3-D vestibular sensation," IEEE Transactions on Biomedical Engineering, vol. 54, No. 6 2007.

Della Santina et al., "Current and future management of bilateral loss of vestibular sensation—an update on the Johns Hopkins multichannel vestibular prosthesis project," Cochlear Implants International, (in press) Sep. 2010).

Della Santina et al., "Electrical stimulation to restore vestibular function—development of a 3-D vestibular prosthesis," IEEE, Shanghai, China: 2005.

Fridman et al., "Multichannel Vestibular Prosthesis Stabilizes Eyes for Head Rotation About Any Axis," Journal of the Association for Research in Otolaryngology, vol. Submitted 2009, Feb. 2010 (Abstract).

Gong et al., "Prototype neural semicircular canal prosthesis using patterned electrical stimulation," Ann Biomed Eng, vol. 28, No. 5 2000.

Gong et al., "System design and performance of a unilateral horizontal semicircular canal prosthesis," IEEE Transactions on Biomedical Engineering, vol. 49, No. 2 2002.

Gong et al., "Vestibulo-Ocular Responses Evoked Via Bilateral Electrical Stimulation of the Lateral Semicircular Canals," IEEE Transactions on Biomed. Engin., vol. 55, No. 11 2008.

Jiang et al., IEEE Transactions on Biomedical Circuits and Systems, vol. 5, No. 2, Apr. 2011.

Lewis et al., "Cross-axis vestibular adaptation produced by patterned electrical stimulation," Neurology, vol. 56, No. 8 2001.

Lewis et al., "Vestibular adaptation studied with a prosthetic semicircular canal," Journal of Vestibular Research—Equilibrium & Orientation, vol. 12, No. 2-3 2002.

Merfeld et al., "Acclimation to chronic constant-rate peripheral stimulation provided by a vestibular prosthesis," IEEE Transactions on Biomedical Engineering, vol. 53, No. 11 2006.

Merfeld et al., "Chronic vestibuloocular reflexes evoked by a vestibular prosthesis," IEEE Transactions on Biomedical Engineering, vol. 54, No. 6 2007.

Van Den Bosch et al., "An Accurate Yield Model for CMOS Current-Steering D/A Converters," Analog Integrated Circuits and Signal Processing 29, 173-180 Kluwer, 2001.

Dommel et al., "A CMOS retinal neurostimulator capable of focused, simultaneous stimulation," J Neural Eng. Jun. 2009;6(3):035006.

International Search Report and Written Opinion of PCT/US2011/045384 Apr. 6, 2012.

* cited by examiner

*Primary Examiner* — George Manuel
(74) *Attorney, Agent, or Firm* — Venable LLP; Henry J. Daley

(57) ABSTRACT

A multichannel vestibular prosthesis includes a sensor system and a microcontroller configured to communicate with the sensor system to receive sensor signals from the sensor system while in operation. The microcontroller is configured to provide control signals in response to the sensor signals. The multichannel vestibular prosthesis also includes a neuroelectronic interface integrated circuit configured to communicate with the microcontroller to receive the control signals, and a plurality of electrodes electrically connected to the neuroelectronic interface integrated circuit. The neuroelectronic interface integrated circuit includes a digital controller configured to communicate with the microcontroller, a plurality of digital-to-analog converters configured to communicate with the digital controller, and a plurality of analog current control circuits, each constructed to communicate with a respective one of the plurality of digital-to-analog converters. Each of the plurality of analog current control circuits can be electrically connected directly or under software control to a respective one of a plurality of electrodes for delivering electrical stimuli to at least one vestibular nerve, and the digital controller is configured to control amplitudes, frequencies, polarities and durations of currents to be delivered to any combination of the plurality of electrical leads.

29 Claims, 3 Drawing Sheets

HIGH-VOLTAGE CMOS NEUROELECTRONIC INTERFACE FOR A MULTICHANNEL VESTIBULAR PROSTHESIS

CROSS-REFERENCE OF RELATED APPLICATION

This application claims priority to U.S. Provisional Application No. 61/367,474 filed Jul. 26, 2010, the entire contents of which are hereby incorporated by reference, and is a U.S. national stage application under 35 U.S.C. §371 of PCT/US2011/045384, filed Jul. 26, 2011, the entire contents of which are incorporated herein by reference.

This invention was made with Government support of Grants No. NIDCD R01DC9255-S21, awarded by the Department of Health and Human Services, NIH. The U.S. Government has certain rights in this invention.

BACKGROUND

1. Field of Invention

The field of the currently claimed embodiments of this invention relates to multichannel vestibular prosthesis and to application specific integrated circuits (ASICs) for vestibular prostheses.

2. Discussion of Related Art

In normal individuals, sensory endorgans within the labyrinth in each inner ear modulate activity on afferent fibers of each of 5 vestibular nerve branches in order to provide the central nervous system with sensation of rotational head motion and gravitoinertial linear acceleration (J. P. Carey and C. C. Della Santina, "Principles of applied vestibular physiology,". C. W. Cummings, Ed. Elsevier, 2005). Vestibular sensory input drives compensatory reflexes that stabilize gaze and posture to maximize clarity of vision during head movements and to prevent falls. Individuals who have suffered damage to their vestibular organs, commonly due to ototoxic medications, experience disabling loss of visual acuity and balance (C. C. Della Santina, A. A. Migliaccio, R. Hayden, T. A. Melvin, G. Y. Fridman, B. Chiang, N. S. Davidovics, C. Dai, J. P. Carey, L. B. Minor, I. C. W. Anderson, H. Park, S. Lyford-Pike, and S. Tang, "Current and future management of bilateral loss of vestibular sensation—an update on the Johns Hopkins multichannel vestibular prosthesis project," Cochlear Implants International, (in press) 2010).

Recently, interest has grown in creating vestibular prostheses that can restore lost function to severely affected patients, much as a cochlear implant restores auditory input to the deaf and severely hard of hearing. Several promising studies using a single-channel device have been reported. See the following for some examples:

W. S. Gong and D. M. Merfeld, "Prototype neural semicircular canal prosthesis using patterned electrical stimulation," Ann Biomed Eng, vol. 28, no. 5 2000.

W. S. Gong and D. M. Merfeld, "System design and performance of a unilateral horizontal semicircular canal prosthesis," IEEE Transactions on Biomedical Engineering, vol. 49, no. 2 2002.

D. M. Merfeld, W. S. Gong, J. Morrissey, M. Saginaw, C. Haburcakova, and R. F. Lewis, "Acclimation to chronic constant-rate peripheral stimulation provided by a vestibular prosthesis," IEEE Transactions on Biomedical Engineering, vol. 53, no. 11 2006.

D. M. Merfeld, C. Haburcakova, W. Gong, and R. F. Lewis, "Chronic vestibulo-ocular reflexes evoked by a vestibular prosthesis," IEEE Transactions on Biomedical Engineering, vol. 54, no. 6 2007.

W. S. Gong, C. Haburcakova, and D. M. Merfeld, "Vestibulo-Ocular Responses Evoked Via Bilateral Electrical Stimulation of the Lateral Semicircular Canals," IEEE Transactions on Biomedical Engineering, vol. 55, no. 11 2008.

R. F. Lewis, D. M. Merfeld, and W. S. Gong, "Cross-axis vestibular adaptation produced by patterned electrical stimulation," Neurology, vol. 56, no. 8 2001.

R. F. Lewis, W. S. Gong, M. Ramsey, L. Minor, R. Boyle, and D. M. Merfeld, "Vestibular adaptation studied with a prosthetic semicircular canal," Journal of Vestibular Research-Equilibrium & Orientation, vol. 12, no. 2-3 2002.

A Stimulator ASIC Featuring Versatile Management for Vestibular Prostheses

Dai Jiang, *Member, IEEE*, Andreas Demosthenous, *Senior Member, IEEE*, Timothy A. Perkins, Xiao Liu, *Member, IEEE*, and Nick Donaldson, IEEE TRANSACTIONS ON BIOMEDICAL CIRCUITS AND SYSTEMS, VOL. 5, NO. 2, April 2011

Because the normal vestibular labyrinth senses head movement in all 3 directions, we have extended this approach to a multichannel vestibular prosthesis (MVP) that modulates activity of surviving vestibular afferent fibers in 3 ampullary nerves that normally encode each of 3 components of head rotation. See the following:

C. C. Della Santina, A. A. Migliaccio, and A. H. Patel, "Electrical stimulation to restore vestibular function—development of a 3-D vestibular prosthesis," Shanghai, China: 2005.

C. C. Della Santina, A. A. Migliaccio, and A. H. Patel, "A multichannel semicircular canal neural prosthesis using electrical stimulation to restore 3-D vestibular sensation," IEEE Transactions on Biomedical Engineering, vol. 54, no. 6 2007.

G. Y. Fridman, N. Davidovics, C. Dai, and C. C. Della Santina, "Multichannel Vestibular Prosthesis Stabilizes Eyes For Head Rotation About Any Axis," Journal of the Association for Research in Otolaryngology, vol. Submitted 2009, 2009.

B. Chiang, G. Y. Fridman, and C. C. Della Santina, "Enhancements to the Johns Hopkins Multi-Channel Vestibular Prosthesis Yield Reduced Size, Extended Battery Life, Current Steering and Wireless Control," presented at Association for Research in Otolaryngology Abst. 867, Baltimore, Md. 2009.

N. S. Davidovics, G. Y. Fridman, B. Chiang, C. C. Della Santina, "Effects of biphasic current pulse frequency, amplitude, duration and interphase gap on eye movement responses to prosthetic electrical stimulation of the vestibular nerve," IEEE Trans Neural Syst Rehabil Eng. 2011 February; 19(1):84-94.

Previous iterations of our MVP design have successfully restored vestibular reflexes in animal experiments, providing strong support for the promise of MVPs improving quality of life for vestibular-deficient individuals. However, to date, there still remain no fully functional, fully implantable vestibular prostheses. There thus remains a need for improved vestibular prostheses.

SUMMARY

A multichannel vestibular prosthesis according to an embodiment of the current invention includes a sensor system and a microcontroller configured to communicate with the sensor system to receive sensor signals from the sensor system while in operation. The microcontroller is configured to provide control signals in response to the sensor signals. The multichannel vestibular prosthesis also includes a neuroelectronic interface integrated circuit configured to communicate with the microcontroller to receive the control signals, and a plurality of electrodes electrically connected to the neuroelectronic interface integrated circuit. The neuroelectronic interface integrated circuit includes a digital controller configured to communicate with the microcontroller, a plurality of digital-to-analog converters configured to communicate with the digital controller, and a plurality of analog current control circuits, each constructed to communicate with a respective one of the plurality of digital-to-analog converters. Each of the plurality of analog current control circuits can be electrically connected directly or under software control to a respective one of a plurality of electrodes for delivering electrical stimuli to at least one vestibular nerve, and the digital controller is configured to control amplitudes, frequencies, polarities and durations of currents to be delivered to any combination of the plurality of electrical leads.

A neuroelectronic interface integrated circuit for a multichannel vestibular prosthesis according to an embodiment of the current invention includes a digital controller configured to communicate with or perform the role of a microcontroller of the vestibular prosthesis; a plurality of data converters (digital to analog and analog to digital) configured to communicate with the digital controller; and a plurality of analog current control and conditioning circuits (amplifiers and filters), each constructed to communicate with a respective one of the plurality of digital-to-analog converters. Each of the plurality of analog current control circuits is electrically connected to a respective one of a plurality of electrodes for delivering electrical stimuli to at least one vestibular nerve, and the digital controller is configured to control amplitudes, polarities and durations of currents to be delivered to any combination of the plurality of electrical leads.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of the current invention can provide a multichannel vestibular prosthesis (MVP) architecture that includes motion sensing circuitry, a microcontroller, power circuitry, and a neuroelectronic interface (NEI). In the context of this architecture, the NEI is configured to drive any combination of 16 electrodes with a programmable current. The stimulation current magnitude, direction, and timing are controlled by the combination of the digital controller and the microcontroller. The NEI is also configured to monitor the potential across any two electrodes for diagnostic purposes (e.g., for electrophysiologic monitoring of vestibular nerve responses, to measure electrode impedances, or to provide real-time feedback to ensure stimuli adhere to safe stimulation criteria). In the MVP1 (C. C. Della Santina, A. A. Migliaccio, and A. H. Patel, "A multichannel semicircular canal neural prosthesis using electrical stimulation to restore 3-D vestibular sensation," IEEE Transactions on Biomedical Engineering, vol. 54, no. 6 2007) and MVP2 (B. Chiang, G. Y. Fridman, and C. C. Della Santina, "Enhancements to the Johns Hopkins Multi-Channel Vestibular Prosthesis Yield Reduced Size, Extended Battery Life, Current Steering and Wireless Control," presented at Association for Research in Otolaryngology Abst. 867, Baltimore, Md. 2009), commercially manufactured stock components are used to realize this interface, at the expense of relatively large consumption of power and circuit space. Some embodiments of the current invention are directed to a reduction of the NEI to a single application specific integrated circuit (ASIC) incorporating several novel features.

MVP electrode impedance and stimulation current output range requirements dictate that the NEI operate at voltages that exceed typical maximum voltages for CMOS processes. This is particularly important because higher electrode compliance voltages allow the use of higher stimulus currents and shorter stimulus pulses that, in turn, allow pulse-frequency modulated stimulation on multiple channels without timing clashes. To achieve compliance voltages of up to 15V, we used the OnSemi C5F/N CMOS process and a design incorporating lightly doped drain (LDD) transistors. However, the concepts of the current invention are not limited to this particular example.

Figure 1:
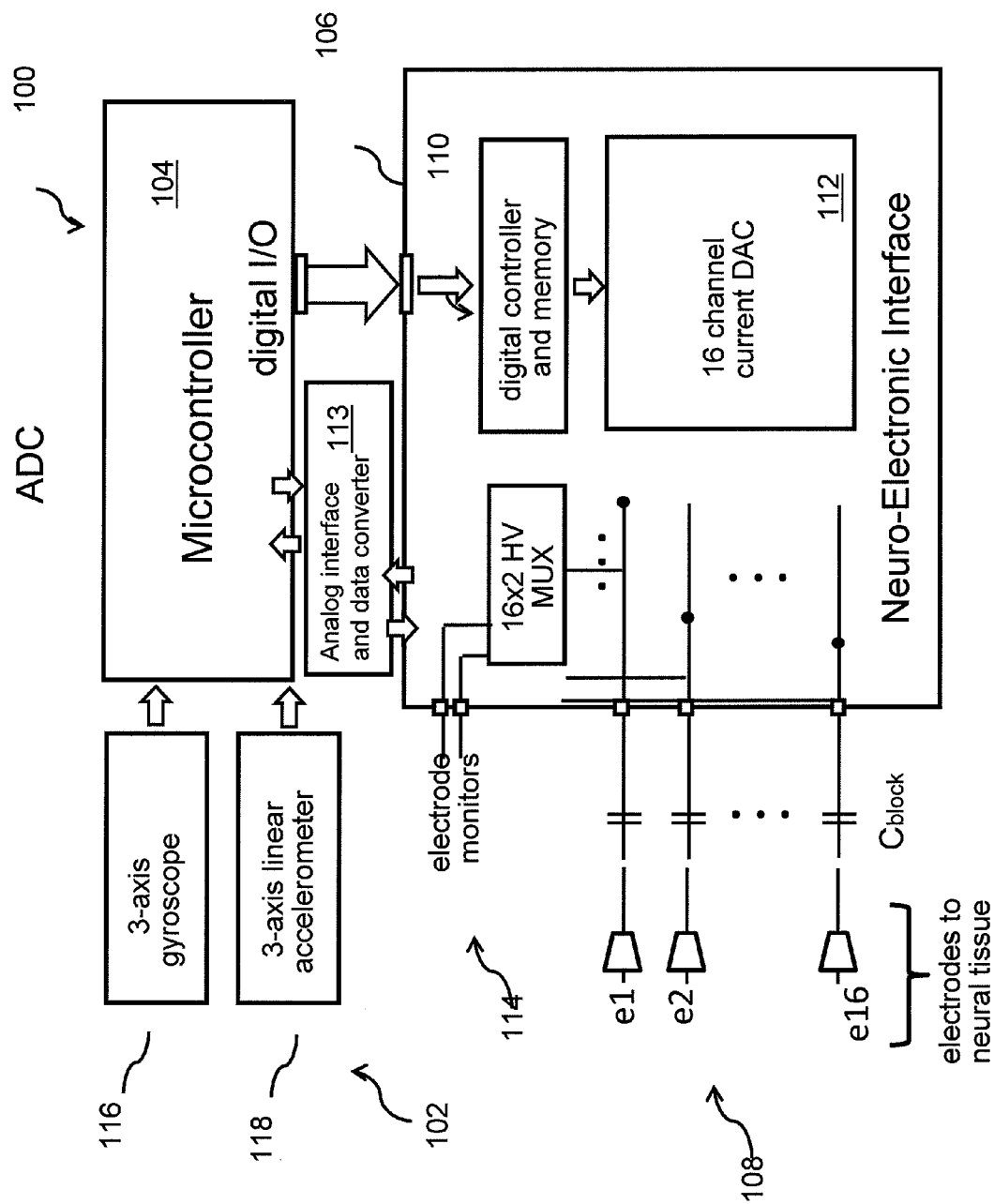
FIG. 1 is a schematic illustration of a Multichannel Vestibular Prosthesis (MVP) architecture according to an embodiment of the current invention.

FIG. 1 is a schematic illustration of a multichannel vestibular prosthesis 100 according to an embodiment of the current invention. The multichannel vestibular prosthesis 100 includes a sensor system 102, a microcontroller 104 configured to communicate with the sensor system 102 to receive sensor signals from said sensor system while in operation. The microcontroller 104 is configured to provide control signals in response to the sensor signals. The multichannel vestibular prosthesis 100 also includes a neuroelectronic interface integrated circuit 106 configured to communicate with the microcontroller 104 to receive the control signals, and a plurality of electrodes 108 electrically connected to the neuroelectronic interface integrated circuit 106. The neuroelectronic interface integrated circuit 106 includes a digital controller 110 configured to communicate with the microcontroller 104. The neuroelectronic interface integrated circuit 106 also includes a plurality of analog conditioning and data converters 113 converters configured to communicate with the digital controller and a plurality of analog current control circuits 112. Each of the plurality of analog current control circuits 112 is constructed to communicate with a respective one of the plurality of data converters. Each of the plurality of analog current control circuits is also electrically connected to a respective one of the plurality of electrodes 108 for delivering electrical stimuli to at least one vestibular nerve. The digital controller 110 is configured to control amplitudes, polarities and durations of currents to be delivered to any combination of the plurality of electrical leads.

In an embodiment of the current invention, the digital controller 110 can be adapted to selectively provide control signals for at least one of monopolar, bipolar, or multipolar stimulation to a selected vestibular nerve. According to some embodiments of the current invention, the plurality of analog current control circuits can each have a low power standby mode to reduce overall power consumption and to reduce delays and other undesirable effects due to turn-on transients.

According to some embodiments of the current invention, the neuroelectronic interface integrated circuit 106 can be constructed to receive the control signals from the microcontroller 104 at a first operating voltage and provide the analog current at a second operating voltage such that the second operating voltage is higher than the first operating voltage. In some embodiments, the first operating voltage is at least 1 volt and less than 20 volts, and the second operating voltage is at least 2 volts and less than 40 volts. In some embodiments, the first operating voltage is about 5 volts and the second operating voltage is about 15 volts.

According to some embodiments of the current invention, the plurality of analog current control circuits are constructed to provide pulse frequency modulated currents in response to the control signals from the microcontroller 104 and the digital controller/memory 110. According to some embodiments of the current invention, the plurality of analog current control circuits are constructed to provide combined pulse frequency and pulse amplitude modulated currents in response to the control signals from the microcontroller 104 and the digital controller/memory 110.

According to some embodiments of the current invention, the neuroelectronic interface integrated circuit 106 is less than 100 $mm^2$ in size and the multichannel vestibular prosthesis 100 is an implantable multichannel vestibular prosthesis that comprises a single system on a chip (SOC) or a system in a multichip module (MCM) or multiple CMOS dies stacked in 3D technology to conserve both volume and area.

According to some embodiments of the current invention, the plurality of electrodes 108 include at least two electrodes adapted to be electrically connected to the same vestibular nerve and the microcontroller is adapted to direct current to the at least two electrodes in a coordinated manner to control the spatial distribution of current in target tissue. According to some embodiments of the current invention, the plurality of electrodes 108 include at least sixteen electrodes in which three electrodes are structured to be electrically connected to each of the five branches of one vestibular nerve. According to some other embodiments of the current invention, the plurality of electrodes 108 include at least sixteen electrodes in which one or more electrodes are structured to be electrically connected to each of one or more branches of one or both vestibular nerves. An example of electrodes that can be used can be found in PCT/US2011/021005, assigned to the same assignee as the current application, the entire contents of which are incorporated herein by reference. However, the concepts of the current invention are not limited to the use of only those electrodes.

In some embodiments of the current invention, the multichannel vestibular prosthesis 100 can also include a voltage monitoring system 114 to selectively measure a voltage across any subset of the plurality of electrodes during operation of the multichannel vestibular prosthesis.

The sensor system 102 can include a rotational acceleration sensor 116 and a linear acceleration sensor 118 in some embodiments. The rotational acceleration sensor 116 can be, but is not limited to, a three-axis rotational acceleration sensor, and the linear acceleration sensor 116 can be, but is not limited to, a three-axis linear acceleration sensor. The rotational acceleration sensor 116 and the linear acceleration sensor 118 can include micro-electromechanical sensors according to some embodiments of the current invention.

Particular embodiments will now be described in more detail. The general concepts of the current invention are not limited to these particular examples. In a multichannel vestibular prosthesis (MVP) as illustrated in FIG. 1, head motion can be measured by micro-electro-mechanical system (MEMS) gyros and accelerometers chosen for their small size and low power consumption. Motion information can be read by the microcontroller and transformed into a set of neural stimulation pulse train parameters. The microcontroller sets stimulation pulse amplitudes, directions (for anodic or cathodic stimulation), and target electrodes on the fly via a parallel interface during neural stimulation. Multiple stimulation paradigms can be implemented with this system, including monopolar (one electrode with respect to a large-distant reference), bipolar (two active electrodes within the labyrinth), and multipolar arrays that allow enhancement of stimulation selectivity through steering/shaping the current vector field within biologic tissues. To achieve biphasic and charge-balanced pulses required for safe stimulation of neural elements via chronically implanted metal electrodes, the microcontroller reprograms the neuro-electronic interface (NEI) to reverse stimulation polarity after the initial cathodic pulse phase. Pulse timing is controlled through a single slim-enable line from the microcontroller to the NEI. For diagnostic purposes, the microcontroller can connect any two electrodes to a high-impedance buffer on the ASIC via a 16×2 high-voltage multiplexer (MUX) and appropriate analog condition circuits and data converter 113. These signals can be stepped down, filtered and conveyed to the microcontroller's analog input lines by other circuitry on the MVP.

High Compliance Voltage Programmable Current Stimulation

Circuit Description.

Figure 2:
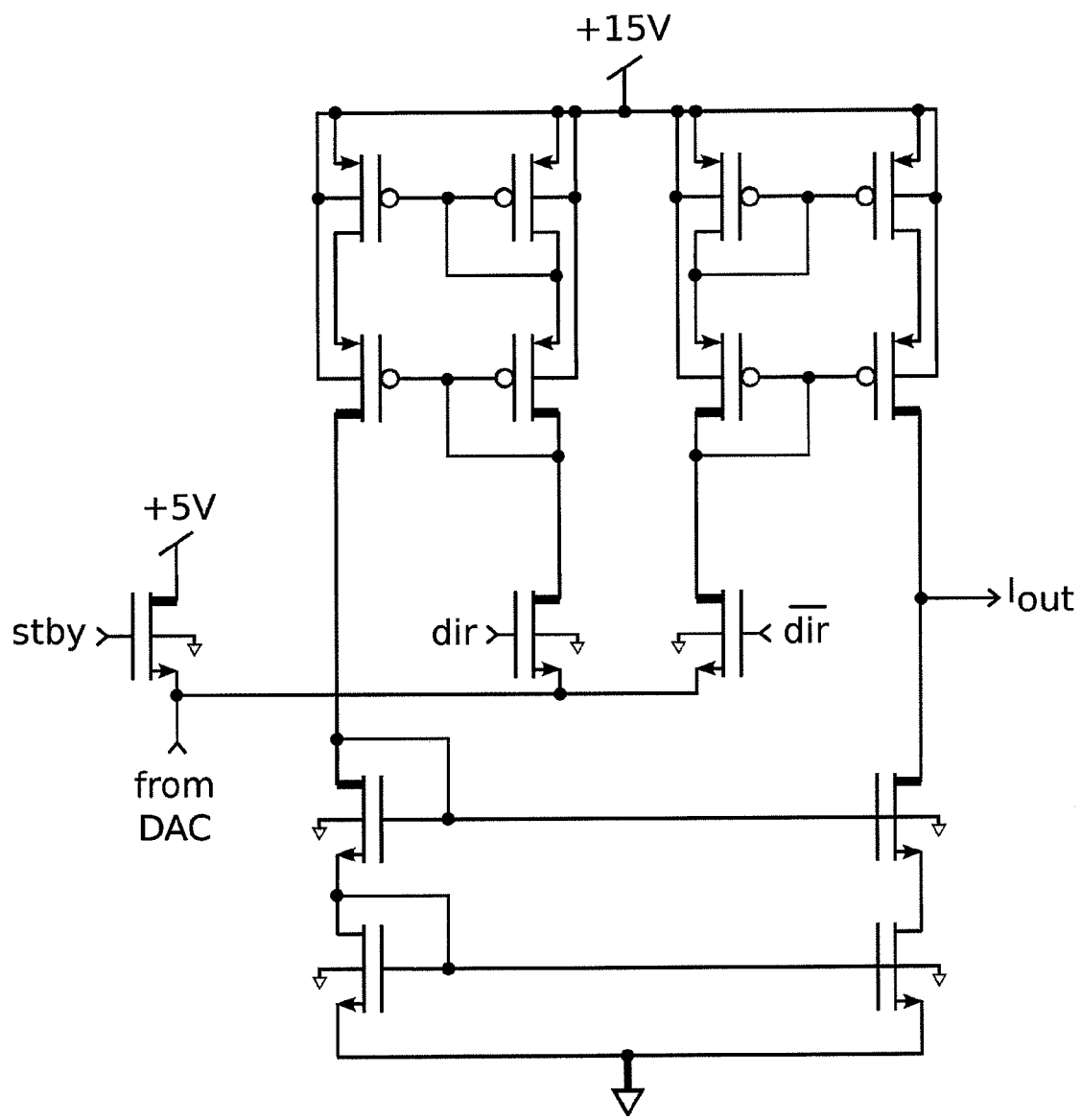
FIG. 2 is a diagram of a high voltage partial current steering circuit with augmented differential pair according to an embodiment of the current invention. High-voltage cascode transistors with lightly doped drains (LDD) (indicated in the schematic by thick lines) are used to protect low-voltage transistors from large voltage swings. The microcontroller can dynamically change dir and stby signals as needed to minimize power consumption.

Each stimulation channel circuit has control registers, a DAC, and a current steering circuit. The DAC is a unary type current source laid out in a common centroid arrangement to minimize mismatch. Current source transistor sizes are computed using a statistical yield model based on fabrication process parameters (A. Van Den Bosch, M. Steyaert, W. Sansen, "An Accurate Yield Model for CMOS Current-Steering D/A Converters," Analog Integrated Circuits and Signal Processing 29, 173-180 Kluwer, 2001). Low-voltage transistors are used in the current source array for optimal matching. Each low voltage current source transistor array is protected from high voltages by an augmented differential pair of the current steering circuit (FIG. 2). The differential pair and standby path transistor are all lightly-doped drain (LDD) high-voltage transistors whose gate signals are constrained to a maximum of 5V, so the maximum voltage the digital-to-analog converter (DAC) encounters during normal operation is 5V.

In order to maximize battery life for an MVP (which includes an implantable battery to ensure continuous function in the event that a user dislodges the external portion of his transcutaneous RF-linked power supply), the NEI is designed to minimize standby and active power consumption. This is achieved through the following design features according to some embodiments of the current invention:

1) During NEI programming, stimulation channels are sequentially programmed by the microcontroller with the desired stimulation current magnitude and direction. To minimize bias current consumption on all channels while any one is being programmed, a partial current steering strategy is employed.

2) The DAC current source for each electrode is kept off unless stimulation is pending on that channel. To avoid delays and turn-on glitches in stimulus current output, the DAC circuit must be charged just before stimulation onset; however, this results in significant power draw from the high-voltage source. Therefore, when a channel is assigned for current stimulation, its DAC is activated and the circuit is put in a standby mode in which the programmed current is directed toward a low-voltage (5V) dummy load. The lower voltage on the dummy path transistor yields lower power consumption in standby mode than would otherwise occur while allowing the DAC current output to relax from charge-up transients.

When the stim-enable signal is received from the microcontroller, the standby circuit path is disabled and one of a differential pair of transistors is activated with a current direction (dir) signal, which chooses either anodic or cathodic current stimulation output. This method of partial current steering has been effectively used to minimize power in similar neural simulators. See, for example:

T. Constandinou and J. Georgiou, "A micropower tilt processing circuit," Baltimore, Md.: 2008.

T. Constandinou, J. Georgiou, and C. Andreou, "An ultra-low-power micro-optoelectromechanical tilt sensor," Seattle, Wash.: 2008.

T. Constandinou, J. Georgiou, C. Doumanidis, and C. Toumazou, "Towards an Implantable Vestibular Prosthesis: The Surgical Challenges," Kohala Coast, Hi.: 2007.

T. Constandinou, J. Georgiou, and C. Toumazou, "A fully-integrated semicircular canal processor for an implantable vestibular prosthesis," St. Julien's: 2008.

T. Constandinou, J. Georgiou, and C. Toumazou, "A Partial-Current-Steering Biphasic Stimulation Driver for Vestibular Prostheses," Biomedical Circuits and Systems, IEEE Transactions on, vol. 2, no. 2 2008.

T. Constandinou, J. Georgiou, and C. Toumazou, "A Neural Implant ASIC for the Restoration of Balance in Individuals with Vestibular Dysfunction," 2009

In the present design, an augmented differential pair amplifier with a wide range output stage enhances the basic "current steering" paradigm for use with higher compliance voltages. Low voltage transistors are used in the current mirrors for their superior matching properties. High voltage cascode transistors are employed to shield low voltage transistors from large voltage swings.

Simulation Results

Simulation results from the high-voltage compliance programmable current stimulator are summarized in Table 1. Simulations were performed using the device checking feature of Cadence in order to monitor over-voltage conditions during transients. DAC NL and DNL were measured at the output of the current steering circuit with a voltage clamp load.

TABLE 1

High-Voltage Compliance Stimulator

| Property | Value | Unit |
|---|---|---|
| Max compliance voltage | 15 | V |
| INL | <0.25 | LSB |
| DNL | <0.2 | LSB |

High Voltage Multiplexed Channel Monitor

Measuring stimulation electrode impedance and monitoring electrically evoked compound action potentials in order to guide electrode placement or monitor afferent nerve fiber health are important functions for an MVP. To provide these abilities, the NEI in this particular embodiment incorporates an analog multiplexer that monitors any 2 of the 16 stimulation channel output voltages. The multiplexer is programmed via the same parallel digital interface used to control stimulus parameters but otherwise operates independently of the stimulation circuitry.

Figure 3:
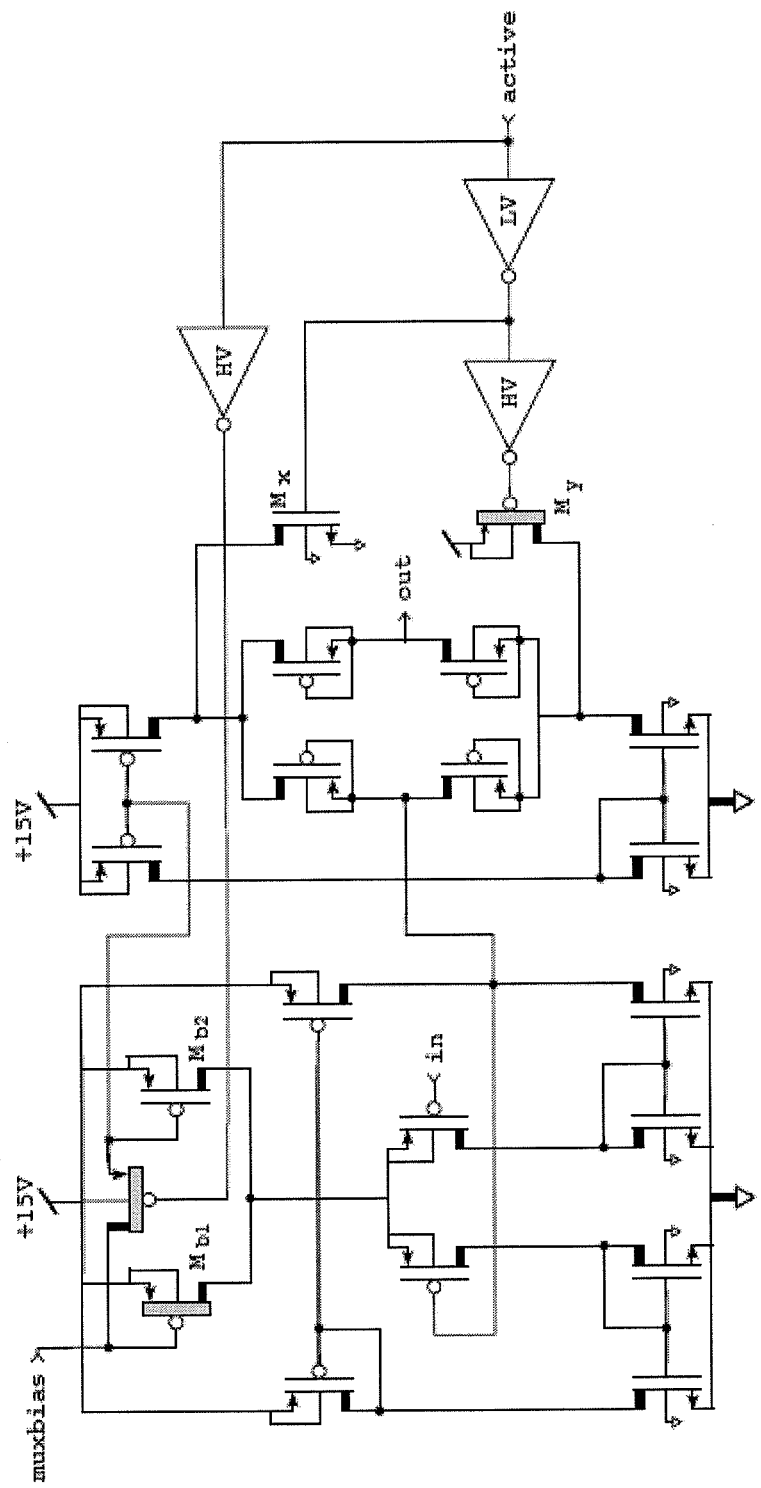
FIG. 3 is a circuit diagram of a multiplexer cell consisting of high-voltage buffer (left) and diode-bridge multiplexer (right) according to an embodiment of the current invention. The control signal active determines the buffer's operating mode (low-power sleep or full-bandwidth buffering). The diode bridge circuit is controlled by the same input signal and is either biased on, or reverse biased.

The analog multiplexer comprises 16 high voltage analog buffers that present a high impedance input to the stimulation channel (FIG. 3). Each electrode is permanently assigned to one corresponding buffer. Considering the voltage range on the stimulation channel outputs, the buffers' input stage must always be biased in order to avoid exceeding gate-bulk voltage limits. However, continuously running each buffer would waste power. Therefore, buffers are powered in two modes that are programmable by the microcontroller: active and sleep. When active, buffers are fully biased in order to meet bandwidth requirements of the stimulation channel signals. When in sleep mode, buffers are biased lower to conserve power, yet they receive enough current to avoid damage from high voltages that could be generated at the stimulation channel output.

Multiplexing buffer outputs onto two output lines is achieved using a diode bridge multiplexer. The diode bridge also has two modes of operation—active and off—that correspond to the buffers' active and sleep modes, respectively. When active, the multiplexer passes the buffer signal to the monitor output line; when off, the diode bridge is reverse biased and presents a high impedance node to both the buffer and the monitor line.

Two transistors are used to bias the buffer: an LDD p-channel Field-effect transistor (PFET, labeled $M_{b1}$), and a thick-gate LDD PFET ($M_{b2}$), which has a higher maximum back gate voltage ($V_{gb}$) and higher threshold voltage. Both transistors receive the same bias voltage, but due to the threshold voltage difference, the thick-gate LDD PFET's drain current is much lower. When the buffer is in sleep mode, it receives bias current only from the thick-gate LDD PFET, which is only 100 nA. When the buffer is active, both bias transistors are turned on for a total bias current of 40 uA.

When multiplexing buffer outputs onto two output lines using a diode bridge multiplexer. The diode bridge also has two modes of operation—active and high-impedance—that correspond to the buffers' active and sleep regimes, respectively. When active, the multiplexer passes the buffer signal to the monitor output line; when in the high-impedance state, the diode bridge is reverse biased and presents a high impedance node to both the buffer and the monitor output line.

The diodes that make up the diode bridge circuit are realized using the lightly doped drain/N-well junction of high voltage (HV) PFETs. Each diode is made of a PFET whose source, gate, and bulk are shorted to the anode, while the LDD acts as the cathode of the diode. The diode bridge is turned off by reversing the polarity of the diodes in the bridge using transistors $M_x$ and $M_y$ (FIG. 3).

Example

System Architecture for a Multichannel Vestibular Prosthesis

The architecture of the multichannel vestibular prosthesis can be optimized for the application at hand. The system is capable of driving a number of electrodes and includes appropriate functional blocks and circuits for closed loop control and calibration as well as adaptation. The vestibular prosthesis relies on the large number of electrodes (16 in our architecture) to help best deliver the electrical signals to interface to the tissue.

This custom integrated circuit is responsible for generating currents of programmable amplitude and polarity and controlled duration into any of 16 electrode channels. It also may provide for voltage monitoring of any two of the electrode channels for measurement of electrically-evoked compound action potentials (eCAPs) or electrode impedances. The electrical specifications have been optimized for the requirements of the multichannel vestibular prosthesis and summarized as follows:

| | |
|---|---|
| Max Current output | 2 mA |
| Output Current Resolution | 9 Bits |
| Relative Accuracy | ±0.25 LSB |
| Differential non-linearity | ±0.1 LSB |
| Offset error | ±1% of Full Scale |
| Gain error | ±0.5% of Full Scale |
| DC Power Supply Rejection Ratio | −60 dB |
| DC Crosstalk | |
| MUX ON resistance | <100 Ω |
| MUX OFF resistance | >1 MΩ |
| AC Characteristics | |
| Output Current Settling Time | 5 µs |
| Current Out Channel Isolation | −90 dB (at 1 kHz) |
| Mux Channel Isolation | −90 db (at 1 kHz) |
| Power Requirements | |
| AVdd—core | 5 V |
| AVdd—output stage | 12 V |
| DVdd—core | 5 V |
| Power dissipation—no current output | 3 mW |

In the above MUX stands for multiplexer, AVdd for analog subcircuitry supply voltage (applied to the drains [hence dd] for transistors in that subcircuit), DVdd for the supply voltage for the digital subcircuit, DC for direct current, and AC for alternating current.

The requirements listed above are chosen in such a way that the power dissipated is minimized while attaining a robust interface to the tissue. However, the general concepts of the current invention are not limited to this particular example.

The maximum voltage swing between any two electrodes is 24 V in this particular embodiment, because we are generating both anodic and cathodic pulses. If we wanted to measure electrode potentials of both polarities, we would need to level shift and divide the signal. In our design, we instead capture the anodic and cathodic pulses independently. This allows us to use only +12 and −12 volts power supplies instead of 24 volts. This 12 volt power supply is chosen as a worst case scenario and smaller power supplies are possible, as low as 5 Volts.

The design of the multiplexer is done is such a way that no level shifter is necessary. However, the DAC must also operate at the high voltages at which the multiplexers operate, so the DAC circuits are designed so that if a DAC's lower rail is at 0 volts, it simply stops sinking current. To accomplish this driving capability, the circuits designed on the single chip NEI application-specific integrated circuits (ASIC) are much more complex than the circuits in the discrete circuitry in prior versions of the multichannel vestibular prosthesis and/or reported in previous work The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A multichannel vestibular prosthesis, comprising:
a sensor system;
a microcontroller configured to communicate with said sensor system to receive sensor signals from said sensor system while in operation, said microcontroller configured to provide control signals in response to said sensor signals;
a neuroelectronic interface integrated circuit configured to communicate with said microcontroller to receive said control signals; and
a plurality of electrodes electrically connected to said neuroelectronic interface integrated circuit,
wherein said neuroelectronic interface integrated circuit comprises:
a digital controller configured to communicate with said microcontroller;
a plurality of digital-to-analog converters configured to communicate with said digital controller; and
a plurality of analog current control circuits, each constructed to communicate with a respective one of said plurality of digital-to-analog converters,
wherein each of said plurality of analog current control circuits can be electrically connected directly or under software control to a respective one of a plurality of electrodes for delivering electrical stimuli to at least one vestibular nerve, and
wherein said digital controller is configured to control amplitudes, frequencies, polarities and durations of currents to be delivered to any combination of said plurality of electrical leads.

2. A multichannel vestibular prosthesis according to claim 1, wherein said digital controller is adapted to selectively provide control signals for at least one of monopolar, bipolar, or multipolar stimulation to a selected vestibular nerve.

3. A multichannel vestibular prosthesis according to claim 1, wherein said plurality of current control circuits each have a low-power standby mode to reduce overall power consumption and to reduce delays and other effects due to turn-on transients.

4. A multichannel vestibular prosthesis according to claim 1, wherein said neuroelectronic interface integrated circuit is constructed to receive said control signals from said microcontroller at a first operating voltage and provide said analog current at a second operating voltage, said second operating voltage being higher than said first operating voltage.

5. A multichannel vestibular prosthesis according to claim 4, wherein said first operating voltage is at least 1 volt and less than 20 volts, and said second operating voltage is at least 2 volts and less than 40 volts.

6. A multichannel vestibular prosthesis according to claim 4, wherein said first operating voltage is about 5 volts and said second operating voltage is about 15 volts.

7. A multichannel vestibular prosthesis according to claim 1, wherein said microcontroller is part of said neuroelectronic interface integrated circuit.

8. A multichannel vestibular prosthesis according to claim 1, wherein said plurality of analog current control circuits are constructed to provide pulse frequency modulated currents in response to said control signals from said microcontroller.

9. A multichannel vestibular prosthesis according to claim 1, wherein said plurality of analog current control circuits are constructed to provide combined pulse frequency and pulse amplitude modulated currents in response to said control signals from said microcontroller.

10. A multichannel vestibular prosthesis according to claim 1, wherein said neuroelectronic interface integrated circuit is less than 100 mm$^2$ in size and said multichannel vestibular prosthesis is an implantable multichannel vestibular prosthesis and is a system on a chip (SOC), in multichip module (MCM) in 2D or 3D CMOS technology.

11. A multichannel vestibular prosthesis according to claim 1, wherein said plurality of electrodes include at least two electrodes adapted to be electrically connected to the same vestibular nerve and said microcontroller is adapted to direct current to said at least two electrodes in a coordinated manner to provide current steering.

12. A multichannel vestibular prosthesis according to claim 1, wherein said plurality of electrodes include at least sixteen electrodes in which one or more electrodes are structured to be electrically connected to each of one or more of the five branches of one or both vestibular nerves.

13. A multichannel vestibular prosthesis according to claim 1, further comprising a voltage monitoring system to selectively measure a voltage across any pair of said plurality of electrodes during operation of said multichannel vestibular prosthesis.

14. A multichannel vestibular prosthesis according to claim 1, wherein said sensor system comprises a rotational acceleration sensor and a linear acceleration sensor.

15. A multichannel vestibular prosthesis according to claim 14, wherein said rotational acceleration sensor is a three-axis rotational acceleration sensor and said linear acceleration sensor is a three-axis linear acceleration sensor.

16. A multichannel vestibular prosthesis according to claim 14, wherein said rotational acceleration sensor comprises at least one micro-electromechanical sensor and said linear acceleration sensor comprises at least one micro-electromechanical sensor.

17. A neuroelectronic interface integrated circuit for a multichannel vestibular prosthesis, comprising:
a digital controller configured to communicate with or perform the role of a microcontroller of said vestibular prosthesis;
a plurality of data converters (digital to analog and analog to digital) configured to communicate with said digital controller; and
a plurality of analog current control and conditioning circuits (amplifiers and filters), each constructed to communicate with a respective one of said plurality of digital-to-analog converters,
wherein each of said plurality of analog current control circuits is electrically connected to a respective one of a plurality of electrodes for delivering electrical stimuli to at least one vestibular nerve, and
wherein said digital controller is configured to control amplitudes, polarities and durations of currents to be delivered to any combination of said plurality of electrical leads.

18. A neuroelectronic interface integrated circuit according to claim 17, wherein said digital controller is adapted to selectively retain in memory and reproduce control signals for at least one of monopolar, bipolar, or multipolar stimulation to a selected vestibular nerve.

19. A neuroelectronic interface integrated circuit according to claim 17, wherein said plurality of analog current control circuits each have a powered standby mode to reduce overall power consumption and to reduce effects due to turn-on transients.

20. A neuroelectronic interface integrated circuit according to claim 17, wherein said digital controller is adapted to communicate with said microcontroller at a first operating voltage and said plurality of current control circuits is adapted to be electrically connected to respective electrical leads at a second operating voltage, said second operating voltage being higher than said first operating voltage.

21. A neuroelectronic interface integrated circuit according to claim 20, wherein said first operating voltage is at least 1 volt and less than 20 volts, and said second operating voltage is at least 2 volts and less than 40 volts.

22. A neuroelectronic interface integrated circuit according to claim 20, wherein said first operating voltage is about 3 to 5 volts and said second operating voltage is about 10 to 15 volts.

23. A neuroelectronic interface integrated circuit according to claim 17, wherein said plurality of analog current control circuits are constructed to be able to provide pulse frequency modulated currents in response to control signals from said microcontroller.

24. A neuroelectronic interface integrated circuit according to claim 17, wherein said plurality of analog current control circuits are constructed to be able to provide combined pulse frequency and pulse amplitude modulated currents in response to control signals from said microcontroller.

25. A neuroelectronic interface integrated circuit according to claim 17, wherein said neuroelectronic interface integrated circuit is less than 100 mm$^2$ in size.

26. A neuroelectronic interface integrated circuit according to claim 17, further comprising a monitoring circuit electrically connected to said plurality of electrodes.

27. A neuroelectronic interface integrated circuit according to claim 17, further comprising an integrated microcontroller with sufficient processing ability and memory to generate, modify, retain and reproduce control signals autonomously.

28. A neuroelectronic interface integrated circuit according to claim 17, further comprising an inductive coupling system for transmission of signals and/or power.

29. A neuroelectronic interface integrated circuit according to claim 17, further comprising a battery, capacitor, or other means of energy storage that allows continued autonomous delivery of stimulation currents to neural tissues despite temporary absence of an external source of power and control signals.

* * * * *

UNITED STATES PATENT AND TRADEMARK OFFICE
CERTIFICATE OF CORRECTION

PATENT NO. : 8,768,484 B2  
APPLICATION NO. : 13/812107  
DATED : July 1, 2014  
INVENTOR(S) : Charles Coleman Della Santina et al.

Page 1 of 1

It is certified that error appears in the above-identified patent and that said Letters Patent is hereby corrected as shown below:

In the Specification

Column 1, Lines 15-18 replace with the following paragraph:
This invention was made with government support under NIDCD R01DC9255-S21, awarded by the Department of Health and Human Services, the National Institutes of Health. The government has certain rights in the invention.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

Page 1 of 1

PATENT NO. : 8,768,484 B2
APPLICATION NO. : 13/812107
DATED : July 1, 2014
INVENTOR(S) : Charles Coleman Della Santina et al.

It is certified that error appears in the above-identified patent and that said Letters Patent is hereby corrected as shown below:

In the Specification

Column 1, Line 15 Insert:
--STATEMENT OF GOVERNMENTAL INTEREST
This invention was made with government support under DC009255, awarded by the National Institutes of Health. The government has certain rights in the invention.--

This certificate supersedes the Certificate of Correction issued November 7, 2017.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*